US006799463B2

(12) United States Patent
Fields et al.

(10) Patent No.: US 6,799,463 B2
(45) Date of Patent: Oct. 5, 2004

(54) METHOD AND SYSTEM FOR AUTOMATED FATIGUE AND STRUCTURAL ANALYSIS OF AN ELEMENT

(75) Inventors: Scott S. Fields, Saint Charles, MO (US); Eric S. Meyer, Chesterfield, MO (US); Jeffrey S. Sermersheim, Saint Charles, MO (US)

(73) Assignee: The Boeing Company, Seattle, WA (US)

( * ) Notice: Subject to any disclaimer, the term of this patent is extended or adjusted under 35 U.S.C. 154(b) by 7 days.

(21) Appl. No.: 10/001,112

(22) Filed: Nov. 2, 2001

(65) Prior Publication Data

US 2003/0088373 A1 May 8, 2003

(51) Int. Cl.[7] .............................. G06F 19/00; G01V 1/28
(52) U.S. Cl. ............................. 73/577; 73/783; 702/42
(58) Field of Search .................. 73/577, 783; 703/1–7; 702/42

(56) References Cited

U.S. PATENT DOCUMENTS

| | | | | |
|---|---|---|---|---|
| 4,858,146 | A | * | 8/1989 | Shebini .......................... 703/1 |
| 6,125,333 | A | * | 9/2000 | Pun ............................. 702/42 |
| 6,212,486 | B1 | * | 4/2001 | Huang et al. .................. 703/7 |
| 6,434,492 | B1 | | 8/2002 | Pollack et al. |
| 2001/0029432 | A1 | * | 10/2001 | Gidwani ....................... 702/15 |
| 2002/0013643 | A1 | * | 1/2002 | Ishii ........................... 700/289 |
| 2002/0112548 | A1 | * | 8/2002 | Dong ........................... 73/850 |
| 2003/0045786 | A1 | * | 3/2003 | Zhao ........................... 600/372 |

* cited by examiner

*Primary Examiner*—Hezron Williams
*Assistant Examiner*—Rose M. Miller
(74) *Attorney, Agent, or Firm*—Alston & Bird LLP

(57) ABSTRACT

A method, system and computer program product are provided for automated fatigue and structural analysis of a structural element. The method, system and computer program product consolidate and manage the fatigue and structural analysis tools and are responsive to user requests for fatigue and structural analysis of elements based upon user-provided information regarding the element. As such, the appropriate fatigue and structural analysis tools are automatically selected and run, and the output of the tools is automatically evaluated to provide immediately useful fatigue and structural analysis results to the user without requiring further manual input. Thus, people without specialized training can quickly obtain fatigue and structural analysis results for an element. In addition, because the fatigue and structural analysis tools are integrated, the tools may be accessed from remote locations via a computer network.

16 Claims, 11 Drawing Sheets

METHOD AND SYSTEM FOR AUTOMATED FATIGUE AND STRUCTURAL ANALYSIS OF AN ELEMENT

FIELD OF THE INVENTION

This invention relates to fatigue and structural analyses and, more particularly, to a method, system and computer program product, typically embodied in an Internet-based solution, that provides for automated fatigue and structural analysis to generate results, such as margins of safety.

BACKGROUND OF THE INVENTION

Structural components such as airframes, automobiles, bridges, etc., are subjected to various types of forces throughout their intended design life. These forces create stresses in the structure that can eventually cause wear, damage, and the possible failure of the structure. As such, fatigue and structural analysis of many structural components (structural components is also referred herein as structural elements or elements) is important during the design process. Fatigue and structural analyses provide structural designers with critical information used to determine the likelihood and the causes of fatigue related structural failures. Once the structural designers have the results of the fatigue and structural analyses, they can design the individual elements and the overall structure so as to withstand the anticipated stress levels over the design lifetime.

Fatigue and structural analyses are particularly important for structures that are subject to extreme forces over the lifetime of the structure. For instance, aircraft structures experience a variety of intense forces as they repeatedly take off, fly, perform various maneuvers and land over the lifetime of the aircraft. These forces create stresses internally in the structure, which may cause wear, damage, and possible failure of the structure if it is not properly designed to withstand the anticipated stresses.

In general, fatigue and structural analyses are performed using a series of analysis tools. The tools typically include customized computer programs for a specific structural design (e.g., an F-15 fighter aircraft). The programs typically do not interact with each other directly and are often hosted on computer platforms that cannot communicate with one another. As such, specially trained analysts must be involved throughout the design process to check, modify, and translate the inputs and outputs of each computer program. The fatigue and structural analysis process is time consuming and inefficient because designers must delay their structural design work until specially trained fatigue analysts develop "fatigue allowables" (the maximum repeated stress a structural component can withstand without failure) for each specific structural element. Development of the fatigue allowables is time consuming because it involves determining the anticipated loading throughout each component's design life, generating the fatigue life prediction of each component based on the loading and material properties of the component, and relaying this information back to the structural designer. The designer must then compute the maximum stress in the component based on its current configuration and compare that stress to the fatigue allowable. If the component is determined to have an inadequate fatigue life, the designer must change the configuration of the component and repeat the maximum stress analysis process.

The fatigue and structural analysis processes used in the past are also inflexible because they are tailored to specific computer platforms. And, typically, there are multiple computing platforms involved in the process requiring translation of intermediate results to different computer platforms that are not compatible with one another. For example, when developing the fatigue allowables, different computer applications are generally required to determine the anticipated loading throughout each component's design life, generate the fatigue life prediction of each component based upon the loading and material properties of the component, and compute the maximum stress in the component based upon its current configuration.

For the reasons discussed above, there exists a need for an automated fatigue and structural analysis system that combines and manages the separate fatigue and structural analysis tools such that analysts without specialized training and on various computer platforms may quickly obtain useful fatigue and structural analysis results. Specifically, the need is for a fatigue and structural analysis system that automatically accesses and runs the appropriate fatigue and structural analysis tools to quickly analyze user-provided information regarding a structural component and provide an immediate report of the fatigue and structural analysis results without further manual input.

SUMMARY OF THE INVENTION

In accordance with the present invention, a method, system and computer program product, typically embodied as an Internet-based solution, are provided for automated fatigue and structural analyses. The method, system and computer program product consolidate and manage the fatigue and structural analysis tools and are responsive to user requests for fatigue and structural analyses based upon user-provided information. As such, the method, system and computer program product of the present invention automatically select and run the appropriate fatigue and structural analysis tools, and automatically evaluate the outputs of the tools to provide immediately useful fatigue and structural analysis results to the user without requiring further manual input. Thus, designers without specialized training can quickly obtain fatigue and structural analysis results. In addition, because the method, system and computer program product of the present invention consolidate and manage the fatigue and structural analysis tools, the tools may be accessed from remote locations via the Internet, intranet or other computer network. The method, system and computer program product of the present invention, therefore, save time and increase the efficiency of the design process by opening up the process to designers and eliminating the delay that would otherwise be caused by manually performing fatigue and structural analyses by specially trained analysts.

The method, system and computer program product for automated fatigue and structural analyses of the present invention receive a request to perform fatigue and structural analyses based upon information regarding the structural element of interest. In this regard, the system may include a client component (e.g., a web browser) for receiving the information. Based upon the information regarding the structural element, the method, system and computer program product of the present invention automatically perform the fatigue and structural analyses without requiring further manual input and automatically provide the results of the fatigue and structural analyses. In this regard, the system may also include a processing component (e.g., a server) for automatically performing the fatigue and structural analyses and automatically providing the results of the fatigue and structural analyses to the client component.

Embodiments of the method and system of the present invention also may store the results of the fatigue and structural analyses in a storage element. Other embodiments of the method of the present invention include determining dimensions of the structural element and the material composition of the element based upon the results of the fatigue and structural analyses.

In one advantageous embodiment of the method, system and computer program product of the present invention, the fatigue analysis includes automatically determining a fatigue allowable for the structural element and automatically determining the actual maximum stress in the element. The fatigue allowable for the structural element may be calculated by determining an anticipated loading of the structural element over time and, based upon the anticipated loading of the structural element over time, determining the maximum allowable stress to which the structural element may be subjected. The actual maximum stress for the structural element may be determined by applying a reference load to the structural element to ascertain the actual stress to which the structural element will be subjected. The method, system and computer program product of the present invention then automatically compare the actual maximum stress to the fatigue allowable to determine the margin of safety for the structural element.

The method, system and computer program product of the present invention described herein saves time and increases the efficiency for design processes that require fatigue and structural analyses because the present invention is automated to quickly provide fatigue and structural analysis results. Without the automated features of the present invention, a specially trained analyst would have to manually perform the separate fatigue and structural analyses and manually evaluate the outputs of the analyses to determine and provide the necessary fatigue and structural analysis results before the design process could proceed.

Other useful embodiments of the method, system and computer program product permit the implementation of the present invention via the Internet, intranet or other computer network. Specifically, the system of one embodiment of the present invention includes a client component (e.g., a web browser) and a processing element, such as a server, that are remote from one another and the Internet, intranet or other computer network for interconnecting the client component and the processing element. The system of this embodiment of the present invention may also include a plurality of distributed client components interconnected to the processing elements via the Internet, intranet or other computer network. Regardless of the configuration, each client component may present at least one web page to solicit the required information for fatigue and structural analyses. As such, the required information and the request to perform fatigue and structural analysis may be received from a plurality of distributed clients based upon information input into the respective web pages. The required information and the request to perform fatigue and structural analysis would then be transmitted from the plurality of distributed clients to one or more common processing components via the Internet, intranet or other computer network.

These useful embodiments of the method, system and computer program product of the present invention further reduce the time and increase the efficiency of the design process because they enable the features of the present invention to be performed from different locations via the Internet, intranet or other computer network and in a platform-independent manner. These embodiments are significant improvements over the time consuming and inefficient fatigue and structural analysis previously performed by specially trained analysts on specific workstations with manual evaluation of the results before the design process may proceed.

BRIEF DESCRIPTION OF THE DRAWINGS

Figure 1:
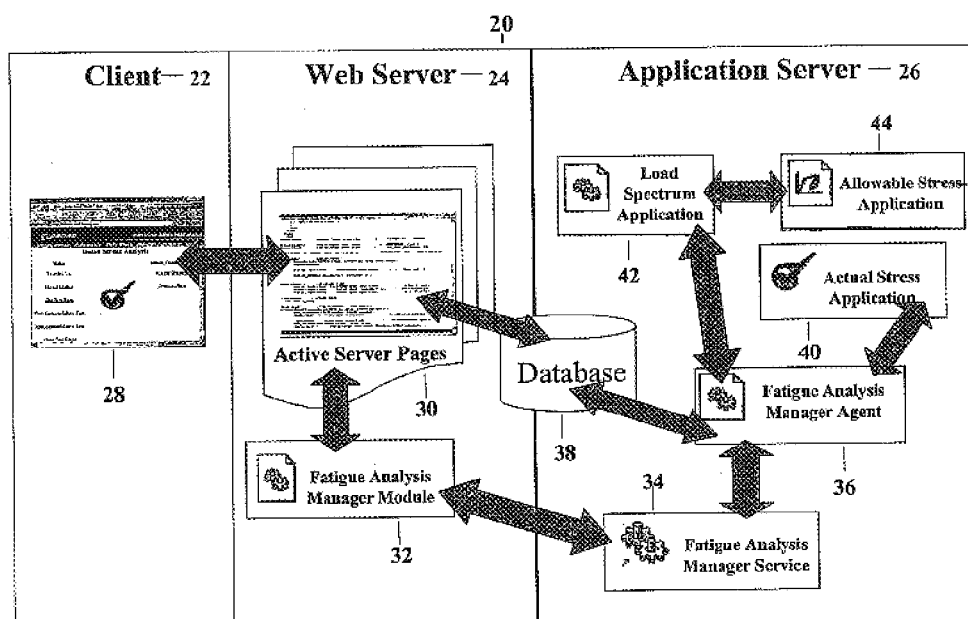
Figure 2:
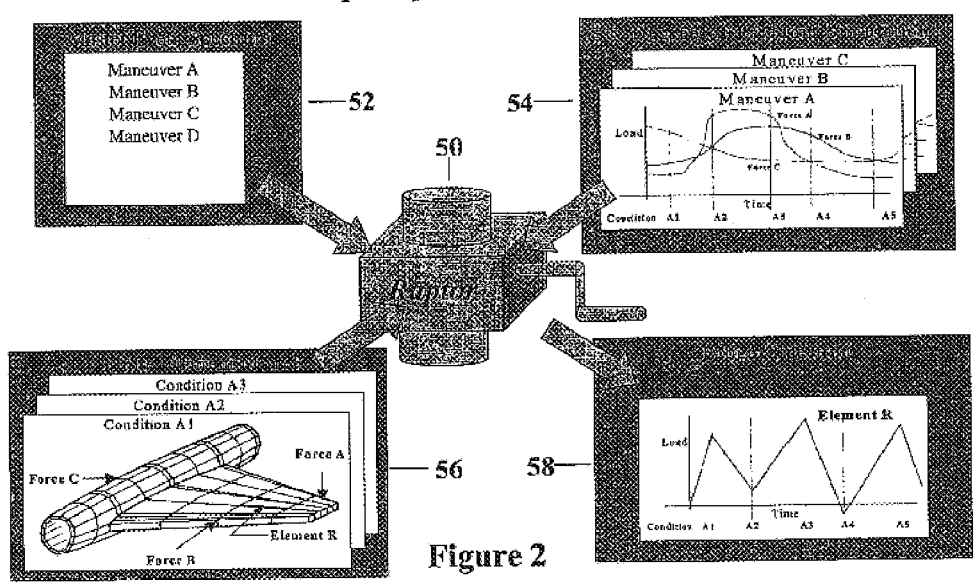
Figure 3:
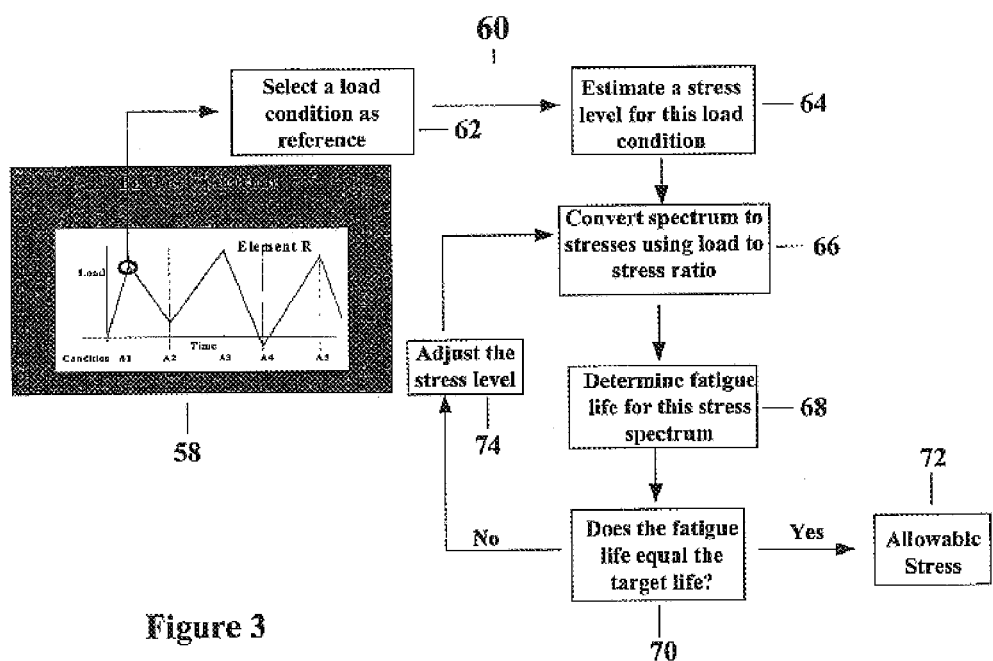
Figure 4:
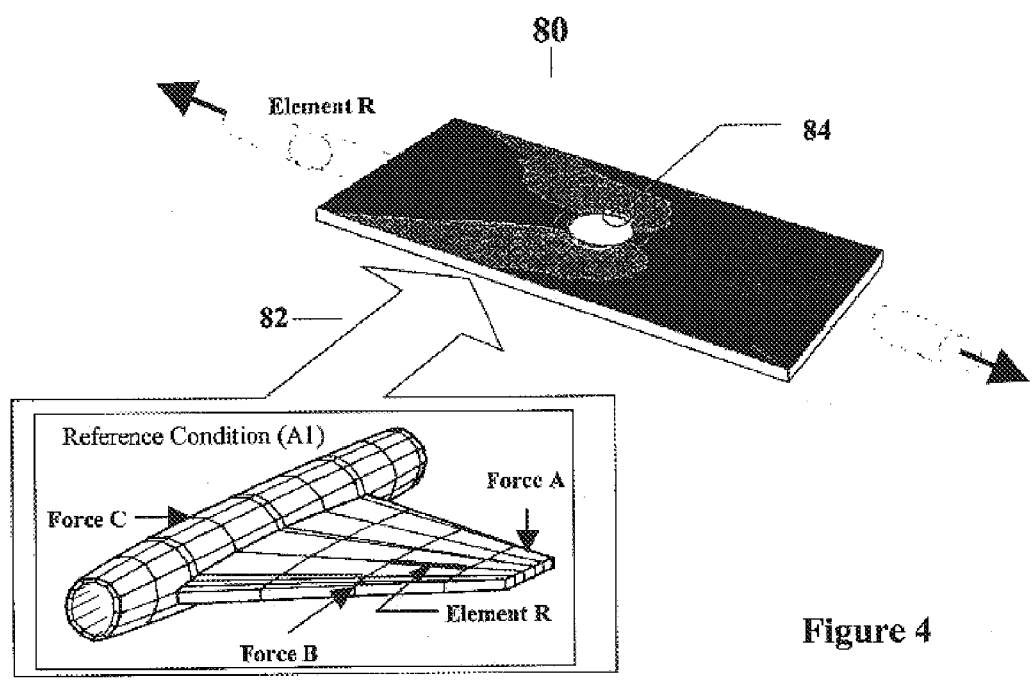
Figure 5:
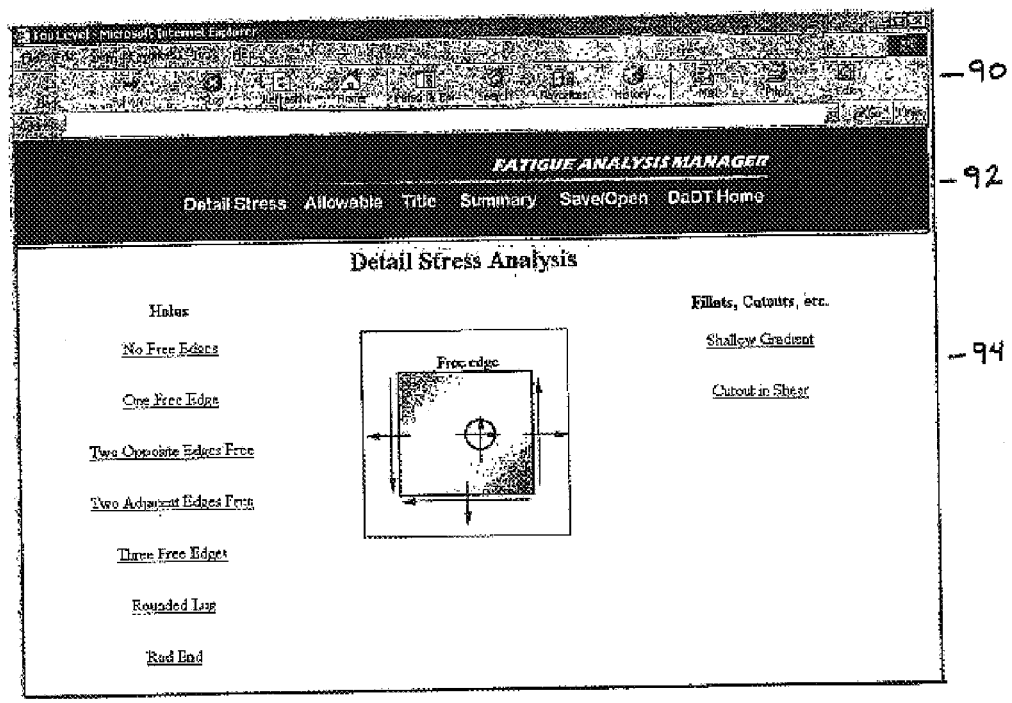
Figure 6:
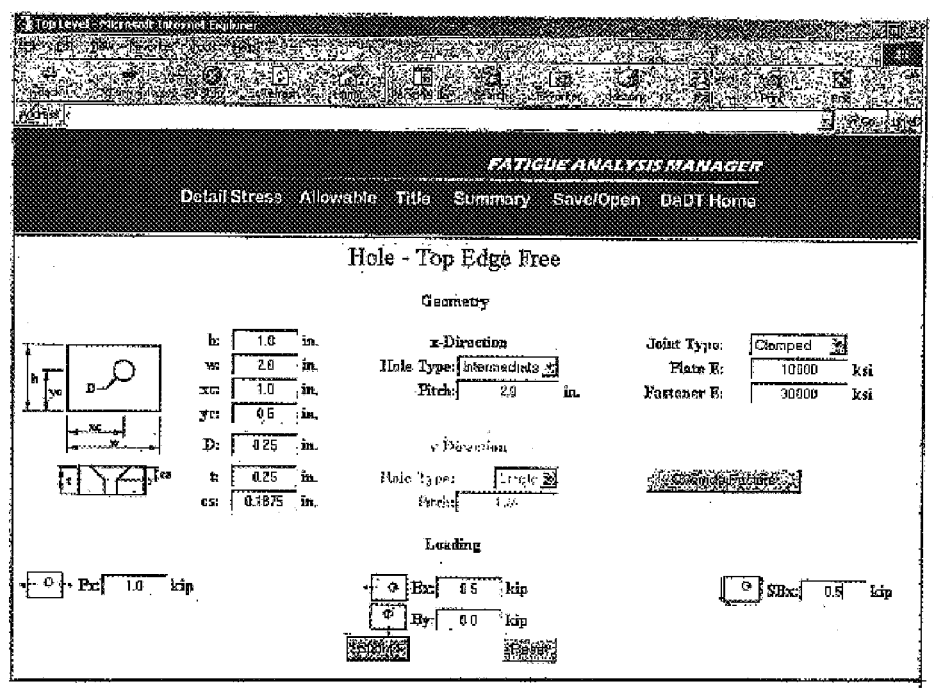
Figure 7:
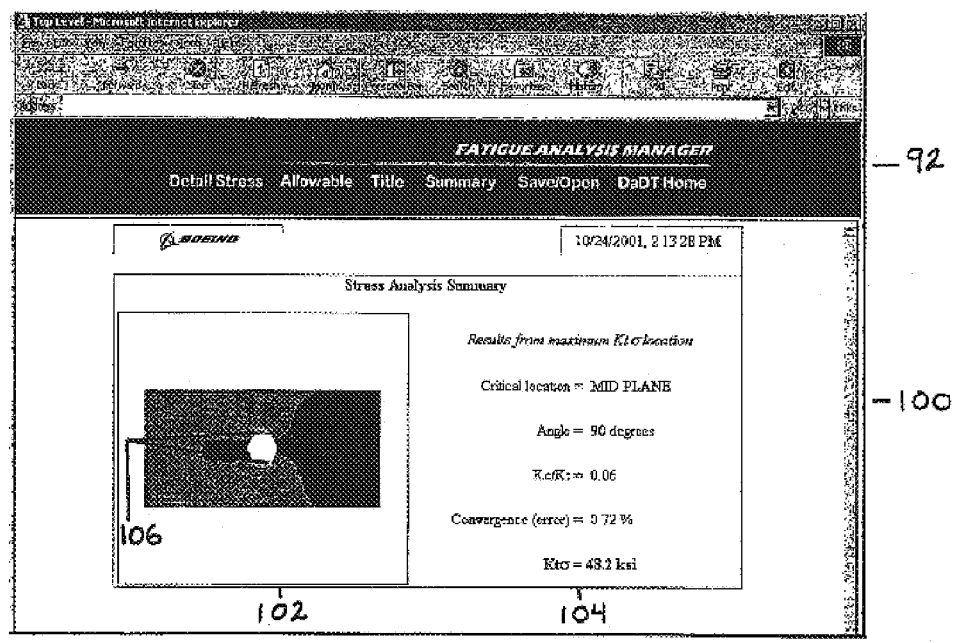
Figure 8:
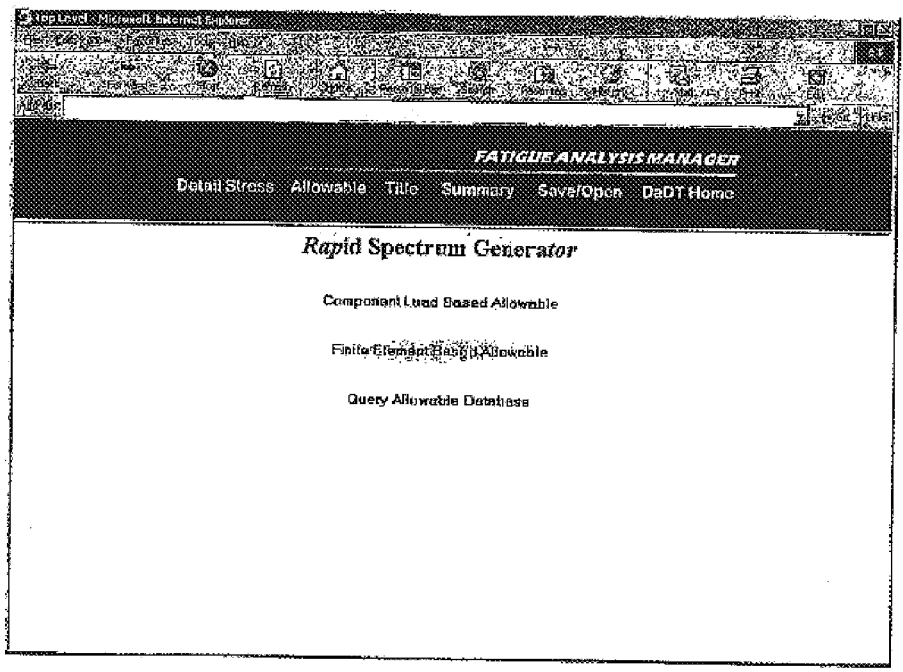
Figure 9:
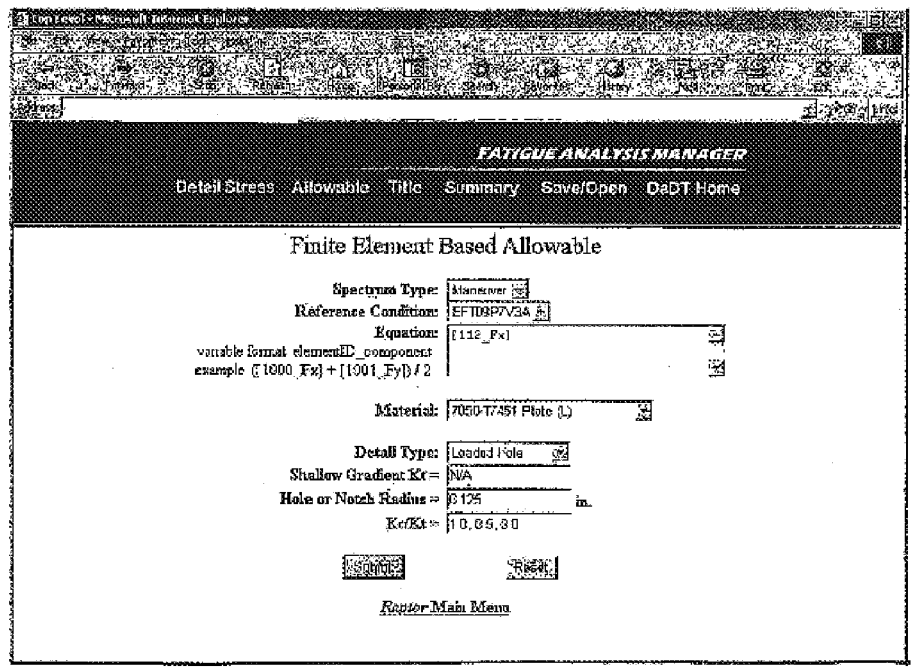
Figure 10:
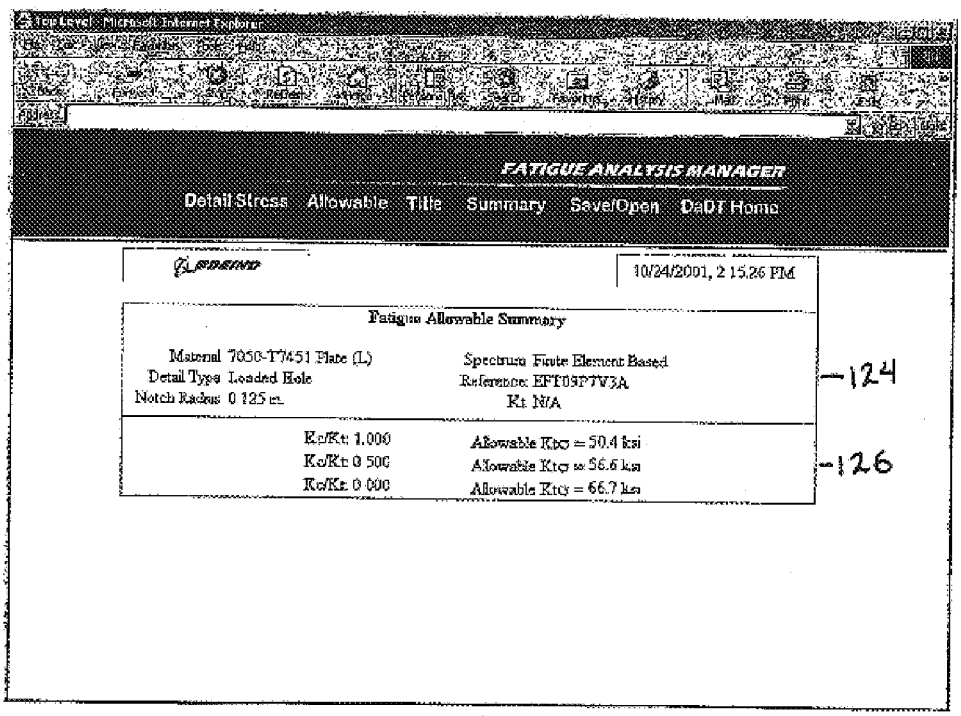
Figure 11:
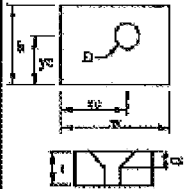

Having thus described the invention in general terms, reference will now be made to the accompanying drawings, which are not necessarily drawn to scale, and wherein:

FIG. 1 is a block diagram illustrating the operations performed by the method, system and computer program product, of one embodiment of the present invention;

FIG. 2 is a flow diagram illustrating the operations of one example of a load spectrum generation application as performed by the method, system and computer program product of one embodiment of the present invention;

FIG. 3 is a flow diagram illustrating the operations of one example of an allowable stress development application as performed by the method, system and computer program product of one embodiment of the present invention;

FIG. 4 is a block diagram illustrating some of the operations of one example of an actual stress development application as performed by the method, system and computer program product of one embodiment of the present invention;

FIG. 5 is a representative display provided by the client interface of the general types of elements on which the detail stress analysis may be performed according to one embodiment of the present invention;

FIG. 6 is a representative display provided by the client interface that prompts the user to input information regarding the element and the reference condition on which actual stress fatigue analysis is requested according to one embodiment of the present invention;

FIG. 7 is a representative display provided by the client interface of the results of the actual stress fatigue analysis that provide the location and measurement of the maximum actual stress experienced by the element at a certain reference condition according to one embodiment of the present invention;

FIG. 8 is a representative display provided by the client interface of the types of allowable stress fatigue analysis that may be performed on an element at a reference condition according to one embodiment of the present invention;

FIG. 9 is a representative display provided by the client interface that prompts the user to input information regarding the element and the reference condition on which finite element based allowable stress fatigue analysis is requested according to one embodiment of the present invention;

FIG. 10 is a representative display provided by the client interface of the results of the allowable stress fatigue analysis at a certain reference condition according to one embodiment of the present invention; and FIG. 11 is a representative display provided by the client interface of the summary of the stress analysis that includes the actual stress fatigue analysis, the allowable stress fatigue analysis, and the margin of safety calculation result according to one embodiment of the present invention.

DETAILED DESCRIPTION OF THE INVENTION

The present invention now will be described more fully hereinafter with reference to the accompanying drawings, in which preferred embodiments of the invention are shown.

This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Fatigue and structural analyses are a fundamental component of the modern structural design process. Structural items such as automobiles, bridges, and aircraft carry loads that vary over time. These structural items are required to operate without failure for a specified life. Performing fatigue and structural analyses allows the structural designer to estimate the life of a structure or to design a structure to meet a required design life.

Fatigue and structural analyses are typically performed for a particular detail within a structural element. Examples of details include fastener holes, cutouts and fillets. As a result of its application to aircraft, the present invention will be primarily described hereinafter in conjunction with fatigue and structural analyses of aircraft. However, the present invention is also useful for the fatigue and structural analysis of a number of other structures as will be apparent to those skilled in the art.

In accordance with the present invention, a method, system and computer program product are provided for automated fatigue and structural analysis of structural elements. The method, system and computer program product consolidate and manage fatigue and structural analysis tools and are responsive to user requests for fatigue and structural analysis based upon user-provided information regarding the structural detail in question. As such, the method, system and computer program product of the present invention automatically select and run the appropriate fatigue and structural analysis tools and automatically evaluate the outputs of the tools to provide immediately useful fatigue and structural analysies results to the user without requiring further manual input. Thus, users without specialized training can quickly obtain fatigue and structural analysis results. In addition, because the method, system and computer program product of the present invention consolidate and manage the fatigue and structural analysis tools, the tools may be accessed from remote locations via the Internet, intranet or other computer network. The method, system and computer program product of the present invention, therefore, save time and increase the efficiency of the design process by eliminating the delay that would otherwise be caused due to manually performing fatigue and structural analyses by specially trained analysts using several separate tools.

FIG. 1 is a block diagram of the method, system 20 and computer program product of one embodiment of the present invention. The system 20 typically includes a client component 22 and a processing component. As shown in FIG. 1, the processing component of one embodiment may have two portions, a web server 24, and an application server 26. The client component and the processing component may be part of a single workstation, computer, server or other computing device and, as such, may communicate with each other via internal transmissions. Alternatively, the client component and the processing component and, in one embodiment, the web server and the application server of the processing component may be distributed as parts of different workstations, computers, servers or computing devices that may be in different physical locations and in communication with each other via the Internet, intranet or other computer network. To be consistent, the discussion herein-after refers to the different components of the system 20 as being distributed, unless otherwise stated. The fatigue analysis system 20 also includes a database 38 that may be part of the client component, the processing component, or most likely, may be separate from both the client and processing components and in communication with one or both of the components via the Internet, intranet or other computer network. Regardless of the configuration, the database 38 is accessed by other parts of the fatigue analysis system 20 via an interface, such as active data object (ADO) interface or open database connectivity (ODBC) interface.

The client component 22 represents the device that includes the interface 28 that users of the automated fatigue analysis system 20 may utilize to request fatigue analysis for a detail of an element (hole, notch, or other structural detail). In the implementation discussed herein, users may request the fatigue allowable, the actual maximum stress in a structural element or the margin of safety. The system could be extended to include automation of any other aspect of fatigue and structural analysis such as sonic fatigue, composite analysis, and buckling. The client component may be a personal computer or workstation operating on any type of computer platform and the interface 28 may be any type of Internet browser. The system 20 may include many client components 22 such that many users may utilize the fatigue analysis system 20. The client component(s) 22 may physically be located anywhere as long as the client component(s) 22 are in communication with the processing component via the Internet, intranet or other computer network.

As described above, the processing element of one advantageous embodiment includes a web server 24, which may utilize any modern operating system, such as Microsoft Windows. Among other functions, the web server 30 provides active server pages 30 to the client component 22, which displays the active server pages 30 for the user via the interface 28. As known to those skilled in the art, the active server pages 30 are interactive forms that prompt the user for the information necessary for the fatigue analysis system 20 to perform fatigue analysis on the structural detail of interest. After the user submits responses to the prompts in the first active server page, the web server 24 determines the content and prompts contained in the successive active server pages based upon the user responses to the prompts contained in the previous active server page or pages.

In the illustrated embodiment, the web server submits the fatigue analysis request to a fatigue analysis manager module 32 via internal server communications, such as via Microsoft's component object module (COM). The fatigue analysis manager module 32 receives the information regarding the element that has been collected by the active server pages 30 and, if necessary, properly formats the information for the fatigue analysis. The fatigue analysis manager module 32 then puts the fatigue analysis request and element information in a queue that is monitored by the application server. The fatigue analysis manager module 32 also monitors the queue for fatigue analysis results posted to the queue by the application server. Once the fatigue analysis manager module 32 identifies that fatigue analysis results have been put in the queue and extracts the fatigue analysis results form the queue, the web server populates or otherwise configures one or more active server pages 30 with the results of the fatigue analysis. The web server then transmits these active web pages to the client component 22 for display to the user via the interface 28.

Although the application server may be configured in different manners, the application server 26 of the illustrated embodiment includes a fatigue analysis manager service 34 and a fatigue analysis manager agent 36. The application server may utilize any modern operating system. The fatigue analysis manager service 34 monitors the queue for fatigue analysis requests placed in the queue by the fatigue analysis manager module 32. The fatigue analysis manager service 34 and the fatigue analysis manager module 32 communicate via any standard queuing technology, such as Microsoft Message Queue (MSMQ). When the fatigue analysis manager service 34 sees a fatigue analysis request in the queue, it delivers the request to the fatigue analysis manager agent 36 via internal server communications, such as via Microsoft's component object module (COM).

The fatigue analysis manager agent 36 receives the fatigue analysis request and the corresponding information regarding the structural detail and determines which fatigue analysis tool(s) to run to perform the desired type of fatigue analysis. The fatigue analysis tools are illustrated as 40, 42, and 44 in FIG. 1 as a specific example that is discussed herein, but any fatigue analysis tool or combination of fatigue analysis tools may be selected and utilized by the fatigue analysis manager agent 36. The fatigue analysis manager agent 36 determines the proper fatigue analysis tool(s) based upon the type of fatigue analysis requested. In this regard, the fatigue analysis manager agent 36 is typically preprogrammed with the fatigue analysis tool(s) to be utilized to perform different types of fatigue analysis. The fatigue analysis manager agent 36 also provides the appropriate fatigue analysis tool(s) with the information regarding the element and receives the output(s) from the fatigue analysis tool(s). The fatigue analysis manager agent 36 communicates with the various fatigue analysis tools that may be located either on the same or other servers or computing devices by any standard inter-machine communication, such as Microsoft's distributed component object module (DCOM).

If the desired type of fatigue analysis requires that the outputs of the fatigue analysis tool(s) be further processed to obtain the fatigue analysis results, then the fatigue analysis manager agent 36 also typically performs those functions. Once the fatigue analysis manager agent 36 determines the fatigue analysis results, whether the results are the direct output of a particular fatigue analysis tool or a computation performed by the fatigue analysis manager agent 36, it stores the results in the database 38, and transmits the results to the fatigue analysis manager service 34. The fatigue analysis manager service 34 then puts the results on the queue for the fatigue analysis manager module 32 to pick up. The active server pages 30 may then be populated or otherwise configured based upon the results prior to being provide to the client component 22 for display to the user via the interface 28. Thus, the method, system and computer program product for automated fatigue and structural analysis of a structural element of the present invention quickly provide users with immediately useful fatigue analysis results for a structural element. In addition, the method, system and computer program product of the present invention enable users, who are not in the same location as the fatigue analysis tools and not trained on the use of the fatigue analysis tools, to obtain the fatigue analysis results that are necessary for a structural design process to proceed in a timely and intuitive manner.

The determination of a fatigue margin of safety is one type of aircraft fatigue analysis that is performed on details within structural elements to determine if the elements can withstand the extreme forces to which the aircraft is subjected over its lifetime. Other types of analyses that could be performed include, for instance, sonic fatigue, buckling, and static strength analysis. In general, margin of safety fatigue analysis is performed by a series of fatigue analysis tools that simulate the forces to which the aircraft is exposed, evaluates the response of the elements to the forces over the lifetime operation of the aircraft, and predicts the life of the structure or calculates an allowable stress. The tools may be a combination of custom built applications for the specific aircraft and separately configured commercial applications. In this regard, although exemplary fatigue analysis tools will be described below for purposes of illustration, it should be understood that those skilled in the art will be familiar with a number of fatigue analysis tools that may be integrated in accordance with the present invention. With respect to a margin of safety, however, the margin of safety equation for a structural element is defined as:

$$\frac{\text{Maximum Allowable Stress}}{\text{Actual Stress}} - 1$$

wherein the maximum allowable stress and the actual stress are determined at the same reference condition for the structural element at issue. The maximum allowable stress is the largest stress that may occur in the structural element without resulting in a premature failure.

FIG. 1 illustrates the communication of the fatigue analysis manager agent 36 with the fatigue analysis tools necessary to perform the margin of safety fatigue analysis for the element. As shown, these fatigue analysis tools are a load spectrum application 42, an allowable stress application 44, and an actual stress application 40. The fatigue analysis manager agent 36 receives the outputs of the fatigue analysis tools 40, 42 and 44 and, based upon the outputs, determines the margin of safety for the element.

The load spectrum application 42 develops a load fatigue spectrum specifically for the structural element of interest. The load spectrum application 42 is typically a computer program developed for the particular type of structure, such as an aircraft, that contains the elements at issue. To develop the load spectrum, information regarding how the structure is utilized over the target life of the structure and estimates of all of the forces to which the structure is subjected by its use are provided to the load spectrum application 42. As described below, the anticipated use of the structure is typically defined by a series of maneuvers or activities, each of which will impose a set of forces upon the structure and, in turn, the elements that make up the structure. In addition, the target life of the structure is the amount of time that the designers of the structure desire the structure to properly function prior to failure. Based upon the combination of forces to which the structure is subjected over time, the load spectrum application 42 then produces the total loads to which the structure is subjected along a time axis that represents the lifetime of the structure.

By way of example, a load spectrum application 42 developed by The Boeing Company called a Rapid Spectrum Generator (Raptor) will be described, although those skilled in the art will be familiar with other suitable load spectrum applications. FIG. 2 is a flow diagram illustrating the operations of the Raptor application 50 to generate a load spectrum 58 for element R, which is an element, i.e., a rod, representing a portion of the wing component of an aircraft. Element R might include a portion of the wing skin, wing spar caps, and webs. To generate the load spectrum 58, the Raptor application 50 first evaluates a master event spectrum 52 for the type of aircraft structure that contains the element R. The master event spectrum 52 for an aircraft is a sequence of maneuvers that the aircraft experiences over the life of the aircraft, such as take offs and landings or any other in-flight movements such as rolls, dives and the like. Based upon the master event spectrum, each maneuver is simulated and the collection of forces to which the aircraft is subjected during each maneuver is captured. For example, the forces on the aircraft 54 during maneuver A are Force A, Force B and Force C. Points in time during the course of performing maneuver A are selected, which are represented as A1, A2, A3, A4 and A5. For each point in time, the load imposed upon element R as a result of the collection of forces upon the aircraft is determined based upon a predefined finite element model 56 for the aircraft. As such, a load spectrum 58 is created for the element R representing the load on element R at each point in time. This load spectrum can be used to determine the fatigue life and margin of safety for any actual structural detail represented by element R.

One example of an allowable stress application 44 uses the load spectrum created by the load spectrum application 42 to determine how much load the structure can withstand over its predefined lifetime prior to failure. Thus, the allowable stress application 44 creates an allowable stress spectrum for the element of the structure based on the load spectrum for the element of the structure.

One type of allowable stress application 44 is the LifeWorks application 60 developed by The Boeing Company, although those skilled in the art will be familiar with other suitable allowable stress applications. To determine the allowable stress for element R, the LifeWorks application 60 selects a reference point, such as load condition A1, and estimates a stress level for the load at time A1. See blocks 62 and 64. The Life Works application 60 then estimates the stress levels for the loads at the other times on the spectrum, A2–A5, by scaling the loads in accordance with the load-to-stress ratio established by the estimated stress level for the load at time A1. See block 66. From the stress spectrum that is created by scaling, the LifeWorks application 60 determines the estimated fatigue life of the element, represented by 68.

If the estimated fatigue life equals the target life of the element, then the estimated stress spectrum is the correct allowable stress spectrum. As mentioned above, the target life of the element is the amount of time that the designers of the structure desire the element of the structure to function prior to failure. If, however, the estimated fatigue life does not equal the target life of the element, then the estimated stress level at condition A1 is adjusted. The resulting stress spectrum is accordingly adjusted based upon the new load-to-stress ratio and the fatigue life is, in turn, determined again. Thus, if the estimated fatigue life is longer than the target life, the estimated stress level at time A1 should be increased, which will accordingly increase the estimated stress spectrum and shorten the estimated fatigue life. If the estimated fatigue life is shorter than the target life, the estimated stress level at time A1 should be decreased, which will accordingly decrease the estimated stress spectrum and lengthen the estimated fatigue life. This type of iterative process, represented by 70 and 74, continues until the estimated stress spectrum results in the estimated fatigue life of the element equaling the target fatigue life of the element or, in some embodiments, exceeding the target fatigue life by no more than a predetermined amount. The resulting stress spectrum is the allowable stress spectrum for the element, represented by 72. Because the allowable stress spectrum is based on the load spectrum 58, it is specific to the particular material and particular element defined by the finite element model 56. The allowable stress spectrum results are transmitted to the fatigue analysis manager agent 36, which may store the results in the database 38 and transmit the results back to the web server and, in turn, the client component via the process described hereinabove.

If the user has requested that the fatigue analysis manager agent 36 determine the margin of safety, the fatigue analysis manager agent 36 will also use the results, in addition to the results from other fatigue analysis tool(s), for the margin of safety calculation. To determine the margin of safety for an element, the fatigue analysis manager agent 36 not only obtains the allowable stress spectrum by utilizing the load spectrum application 42 and the allowable stress application 44, the agent 36 also must obtain the actual maximum stress the element experiences by utilizing the actual stress application 40. The actual stress application 40 may utilize finite element techniques or other automated engineering analysis to calculate the actual stress at various detail locations on the element of the structure. The actual stress application 40 determines the maximum actual stress on the element in response to the imposition of the collection of forces at a particular point in time.

One type of actual stress application 40 is the StressCheck application that is commercially available from Engineering Software Research & Development, Inc. FIG. 4 is a block diagram representation of the operations performed by the StressCheck application 80. The StressCheck application 80 utilizes the collection of forces imposed upon element R at a particular point in time, such as time A1, to determine the actual stresses on a specific structural detail included in element R for that load. This detail might be a fastener hole, a notch, or a fillet. To determine the actual stresses on the detail, the StressCheck application 80 analyzes the geometry of the structural detail represented by element R in detail as the load is applied and creates a detailed representation of the actual geometry and the levels of stress at different locations upon or about element R, as represented by 82. As opposed to the overall or more general analysis of element R provided by the allowable stress application, the StressCheck application can provide the exact location of the maximum stress experienced by the structural element, represented by 84. The actual stress results are transmitted to the fatigue analysis manager agent 36, which may store the results in the database 38 and transmit the results back to the web server and, in turn, the client component via the process described hereinabove. If the user has requested that the margin of safety be determined, the fatigue analysis manager agent 36 will also use the results, in addition to the results from other fatigue analysis tool(s), i.e., from the allowable stress application, for the margin of safety calculation as defined above.

FIGS. 5 through 11 further illustrate the features of the method, system 20 and computer program product of one embodiment of the present invention. The figures demonstrate the embodiment of the present invention that performs automated stress fatigue analysis and margin of safety calculations. In the examples to follow, the figures are representative of the displays of the active server pages 30 that a user may view and with which a user may interact via the interface 28 of the client component 22.

FIG. 5 is a representation of the display 90 via the client interface 28, shown as Microsoft Internet Explorer in this embodiment of the present invention, of an active server page 30 that permits a user to request fatigue stress analysis and margin of safety calculations for an element of a structure. In the upper portion 92 of the display 90, the user may select the type analysis. "Detail Stress" represents a request for an actual stress analysis to determine the maximum actual stress experienced by an element and the location of the maximum actual stress in the element.

"Allowable" represents a request for an allowable stress analysis to determine the allowable stress the element can withstand prior to failure. "Title" permits a user to identify a particular analysis for future reference or the like. "Summary" represents a request for a summary of the types of stress analyses performed on the element and a margin of safety calculation for the element. "Save/Open" represents a request to save or open an existing stress analysis file. "DaDT Home" represents a request to return to a designated home page. The lower portion 94 of the display 90 illustrates the screen when a user selects "Detail Stress" from the upper portion 92. These options are the same in the displays represented in FIGS. 6–10.

The screen of the lower portion 94 permits the user to select the general type of element on which the detail stress analysis is requested. The elements listed will vary based upon, among other factors, the type of structure being analyzed. In this example, however, types of holes, fillets and cutouts contained in the element are listed because the majority of stress damage occurs around these types of openings. When the user brushes over a type of hole, fillet or cutout that is listed with a pointer or cursor, a picture of the type of hole, fillet or cutout is presented on the screen. In FIG. 5, the user brushed over "One Free Edge" listed under "Holes" and a picture showing a hole in an element having one edge without a load is displayed on the screen.

When the user selects "One Free Edge" from the list under "Holes" that is shown in FIG. 5, the web server generates an active server page 30 that is presented to the user as shown in FIG. 6. The screen 96 in FIG. 6 prompts the user to enter information regarding the element for which actual stress fatigue analysis is requested and to define the reference condition for the analysis. The upper left-hand portion of the screen 96 under the "Geometry" heading prompts the user to enter the dimensions of the element and the hole in the element, including the dimensions of the countersink (cs), if any. The upper middle portion of the screen 96 under the "Geometry" heading prompts the user to select and enter information regarding the hole in relation to the existence of other holes. In the "Hole Type" area, the user may choose "Single," "Intermediate," or "End." "Single" indicates that the structural detail has no other hole near the hole in question. "Intermediate" indicates that the hole is somewhere in the middle of a row of holes in the element. "End" indicates that the hole is on the end of a row of holes. If the user selects "Intermediate" or "End" the user must enter the center-to-center spacing between the hole at issue and next closest hole in inches in the "Pitch" area. If appropriate the user can describe the hole in relation to other holes, as described above, in the x-Direction and the y-Direction.

The upper right-hand portion of the screen 96 under the "Geometry" heading prompts the user to select and enter information regarding the fastener, if any, that is in the hole and the material of the element. The "Joint Type" area prompts the user to select "Clamped," "Unclamped," or "N/A." "Clamped" indicates that the hole extends through two plates and a torqued fastener connects the plates through the hole. "Unclamped" indicates that a loose fastener connects two plates through which the hole extends. "N/A" indicates that no fastener is in the hole. The user is also prompted to enter the modulus of elasticity of the element in the "Plate E" area. If the user selected "Clamped" or "Unclamped" in the "Joint Type" area, the user must also enter the modulus of elasticity of the fastener in the "Fastener E" area.

The upper portion of the screen 96 also has a button that the user can select to "Override Factors." The effect of the joint type and hole type is managed through the use of correction factors applied to the results of the StressCheck application 80. These factors are typically determined with the fatigue analysis manager agent 36 based upon closed-form solutions, as known to those skilled in the art. The expert user may override these factors using the override button.

The lower portion of the screen 96 prompts the user for "Loading" information regarding the element with the type of hole indicated. The loading information defines the actual loads that act upon the element at a certain point in time. Thus, the loads entered into the lower portion of the screen 96 define the forces that act upon the element in response to the collection of forces imposed upon the structure at the point in time selected as the reference for the actual stress analysis. Typically, the forces are determined by static analysis external to this method, system, and computer program product using standard methods familiar to those skilled in the art. However, the actual stress application may be designed to determine the forces acting upon the element based upon the collection of forces imposed upon the structure at the point in time selected as the reference for the actual stress analysis. "Px" prompts the user for the forces acting upon the edges of the element in a predefined x-direction. "Bx" and "By" prompt the user for the bearing forces acting upon the periphery of the hole in the x and y directions, respectively. "SBx" prompts the user for the bearing force that acts on the hole in the predefined x-direction and is reacted by shear forces upon the three edges of the element. Depending upon the element, the user may be prompted to provide other forces, such as Py and SBy, in addition to or instead of the forces depicted in FIG. 6.

Once the user selects and enters all of the appropriate information on the display 96, the user may select the "Submit" button, which initiates the automated fatigue analysis for the element as described hereinabove. The fatigue analysis manager agent 36 ultimately receives the user request and element information and automatically selects the fatigue analysis tool to perform the detail stress analysis, which may be an actual stress application 40, such as the StressCheck application 80. When the fatigue analysis manager agent 36 receives the results from the fatigue analysis tool, it stores the results in the database 38 and transmits the results to the fatigue analysis manager service 34 and fatigue analysis manager module 32. The fatigue analysis manager module 32 populates the active server pages 30 with the results for the user to view via the client interface 28.

FIG. 7 represents the display of the results of the stress analysis that the user may receive. The screen 100 depicts the results in two sections, a detailed visual representation of the actual geometry and the various levels of stress at locations upon or about the element, as represented by 102, and textual information regarding the maximum stress and its location, as represented by 104. The detailed visual representation 102 indicates to the user that the greatest levels of stress occur on opposite sides of the hole, i.e., on the top and bottom sides, as indicated by 106. The textual information 104 identifies the section of the element where the maximum stress is located, which is the "MID PLANE" section in this example. The "Angle" value is the angle around the hole from a reference location where the maximum stress is located, which is "90 degrees" in this example, i.e., at the bottom of the hole. The "Kc/Kt" value is the inverse of the absolute value of the ratio of stress resulting from the specified loading to the stress resulting when all specified loads are reversed (applied in the opposite direction). The "convergence (error)" value is a statistical confidence value provided by the fatigue analysis tool. The "Ktσ" value is the maximum actual stress value based on the specified loads for this reference condition.

The user may also request the allowable stress value for the element, if desired, by selecting the "Allowable" button in the upper portion 92 of the display. FIG. 8 is the display generated by the web server and presented by the client component after selecting the "Allowable" button. The display 110 that the user views allows the user to select a type of allowable stress fatigue analysis. For instance, if the load spectrum application 42 and/or finite element model have not yet been developed for the specific structure and elements for which fatigue analysis is desired, the user may select the "Component Load Based Allowable" button. The component load based analysis determines the allowable stress for an element based upon the estimated loads that a component of the structure containing the element experiences. For example, a component of an aircraft may be the wing, tail or part of the body. The user selects and enters information regarding the component that contains the element at issue and also enters the reference value for the analysis. The reference value is a load value that corresponds to the load values provided in the detail stress analysis as described hereinabove. Thus, the component load based analysis is a general analysis of the allowable stress for the component of the structure that contains the element, that may be appropriate in the early stages of the design process before the information needed to generate the load spectrum for the structure is gathered and, perhaps, before a detailed finite element model has been developed.

The display 110 also includes a "Query Allowable Database" button. This option permits the user to query the database 38 that stores the prior-performed allowable stress analyses to determine if the allowable stress analysis results already exist for the element or component at issue and, if so, to retrieve the results of the prior allowable stress analysis.

The user also may select the "Finite Element Based Allowable" button when the load spectrum application 42 and finite element model have been developed for the specific structure and its elements to enable a load spectrum to be generated for the element at issue as explained hereinabove. When the user selects the "Finite Element Based Allowable" button and requests allowable stress analysis, the display shown in FIG. 9 is generated by the web server and provided by the client component on the client interface 28. The display 120 prompts the user to select and enter the information regarding the element for which allowable stress analysis is requested. In the "Spectrum Type" area, the user is prompted to select the type of master events upon which the load spectrum for the particular element is based. Types of spectra include flight maneuvering, taxi and ground handling. These events comprise the master event spectrum 52 as explained. The "Reference Condition" area prompts the user to select a reference condition from the load spectrum for the element, such as the conditions existing at time A1–A5 referred to in the above discussion. The reference conditions may be assigned any type of identifier, such as the "EFT09P7V3A" identifier of the reference condition selected in display 120 which corresponds to the conditions existing at time A1. The reference condition that the user selects may be identical to the reference condition that defines the loading, i.e., the forces, entered in the detail stress analysis. To compare the results of the allowable and the actual stress analysis, such as in a subsequent margin of safety calculation, the actual stress may be ratioed to match the reference condition of the allowable. The "Equation" area of the display 120 permits the user to identify the specific element or elements and load components to be analyzed. For instance, the element at issue in the example shown in FIG. 9 is a rod designated "112" and it carries a load "Fx," which is an axial load only. As known to those skilled in the art, a number of element types are available in finite elements and each element type can carry one or more different types of load, e.g., axial load, shear, moment, or torque. The user can specify any mathematical relation including multiple elements and multiple load components. One example would be to calculate the load spectrum based on the average of several finite elements near the detail of interest. This equation would be of the form $$([101\_Fx]+[102\_Fx]+[103\_Fx]+[104\_Fx])/4$$

wherein 101, 102, 103, and 104 are individual finite elements such as rods or bars. Another example would be a detail that sees stresses that are a function of both axial load and bending moment, "Mx." The exact formulation of the equation would be determined by engineering analysis, as will be apparent to those skilled in the art. An example of this equation would be of the form:

$$0.56*[45\_Fx]+0.123*[45\_Mx]$$

Display 120 further prompts the user to select a material type of the element in the "Material" area. The user then selects the detail type that is located in the element in the "Detail Type" area, which indicates the type of correction factors that the fatigue analysis program may use. If the element contains a shallow gradient, then the stress concentration at the detail is entered in the "Shallow Gradient Kt" area. The radius of the hole or notch, which matches the dimension of the hole entered in display 96 of FIG. 6, is entered in the "Hole or Notch Radius" area of display 120. In addition, the user may define one or more Kc/Kt values. Kc/Kt is defined as the ratio of the stress at a detail under a specified set of loads to the stress at the same detail when the specified set of loads are reversed Alternatively, the web server may generate the active server pages 30 so as to automatically populate the "Detail Type," "Shallow Gradient Kt," "Hole or Notch Radius," and "Kc/Kt" areas based on the information selected and entered for and the results of the detail stress analysis, if available. If the active server pages 30 are automatically populated, the user may nevertheless override those values with manually entered information.

Once the user selects and enters all of the appropriate information on the display 120, the user may select the "Submit" button, which initiates the automated fatigue analysis for the element as described hereinabove. The fatigue analysis manager agent 36 ultimately receives the user request and element information and automatically selects the fatigue analysis tool(s) to perform the allowable stress analysis, which may be an allowable stress application 44, such as the LifeWorks application 60. When the fatigue analysis manager agent 36 receives the results from the fatigue analysis tool, it stores the results in the database 38 and transmits the results to the fatigue analysis manager service 34 and fatigue analysis manager module 32. The fatigue analysis manager module 32 populates the active server pages 30 with the results for subsequent transmission to the client component for the user to view via the client interface 28.

FIG. 10 represents the display of the results of the allowable stress analysis that the user may receive. Display 122 has two portions, the upper portion 124 lists some of the information entered in the display 120 to indicate the parameters that the fatigue analysis tool utilized to reach the results. The lower portion 126 contains the allowable stress (Kt$\sigma$) values for the specified Kc/Kt ratio values.

The user may select the "Summary" button in the upper portion 92 of the display to receive a summary of the stress analyses performed by the automated fatigue analysis method, system and computer program product of one embodiment of the present invention. When the user requests a summary of the stress analyses, the fatigue analysis manager agent 36 automatically determines the margin of safety or any other predefined calculation, using the results of the stress analyses. The display of FIG. 11 is then generated by the web server, transmitted to the client component and presented to the user via the interface 28. The display has four portions, the top portion 128 depicts the information regarding the element and forces acting upon the element that were selected or entered by the user in display 96 of FIG. 6. The next portion 130 depicts the results of the detail stress analysis as shown in display 100 of FIG. 7. A fatigue allowable summary 132, which is also part of the overall summary, is similar to the display 122 of FIG. 10, but the allowable stress result is based on the same Kc/Kt ratio determined in the detail stress analysis, 0.06. Since the allowable stresses were determined at 1.0, 0.5 and 0.0 in this example, the fatigue analysis manager agent 36 performs an iteration to arrive at the allowable stress for 0.06 based upon the allowable stresses at 0.0 and 0.5 Kc/Kt ratios. The stress values used in the margin of safety calculation and the result of the margin of safety calculation performed by the fatigue analysis manager agent 36 are displayed in portion 134. Based upon the results of the fatigue analysis and/or subsequent calculations, such as margin of safety, the designers of the element and structure may adjust the dimensions and/or material composition of the element to produce more desirable fatigue analysis results.

Therefore, the automated fatigue analysis method, system and computer program product of the present invention automatically provide the user with the results of the fatigue analysis tool without requiring any further manual input, that the user be specially trained to use the specific fatigue analysis tool, or that the user be in the same physical location as the fatigue analysis tool.

The system 20 of the present invention and, in particular, the client interface 28, active server pages 30, fatigue analysis manager module 32, fatigue analysis manager service 34, fatigue analysis manager agent 36, database 38, and fatigue analysis tools, are typically embodied by a processing element and an associated memory device, both of which are commonly comprised by a computer or the like. As such, the system of the present invention generally operates under control of a computer program product to provide the functionality described hereinabove in conjunction with the various components of the system, according to another aspect of the present invention. The computer program product for performing the contingent claim valuation includes a computer-readable storage medium, such as the non-volatile storage medium, and computer-readable program code portions, such as a series of computer instructions, embodied in the computer-readable storage medium In this regard, FIGS. 1–4 are block diagrams, flowcharts or other schematic representations of methods, systems and program products according to the invention. It will be understood that each block or step of the flowchart, and combinations of blocks in the flowchart, can be implemented by computer program instructions. These computer program instructions may be loaded onto a computer or other programmable apparatus to produce a machine, such that the instructions which execute on the computer or other programmable apparatus create means for implementing the functions specified in the flowchart block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the flowchart block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the flowchart block(s) or step(s).

Accordingly, blocks or steps of the flowchart support combinations of means for performing the specified functions, combinations of steps for performing the specified functions and program instruction means for performing the specified functions. It will also be understood that each block or step of the flowchart, and combinations of blocks or steps in the flowchart, can be implemented by special purpose hardware-based computer systems which perform the specified functions or steps, or combinations of special purpose hardware and computer instructions.

Many modifications and other embodiments of the invention will come to mind to one skilled in the art to which this invention pertains having the benefit of the teachings presented in the foregoing descriptions and the associated drawings. As such, the Raptor, LifeWorks and StressCheck applications are provided as specific examples of types of fatigue analysis tools, however, the automated fatigue analysis of an element as provided by the method, system and computer program product of the present invention may use other appropriate types of fatigue analysis tools to create the load spectrum, determine the allowable stress and determine the actual stress for an element of an aircraft or other structure in order to perform margin of safety or any other type of fatigue analysis. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for automated fatigue and structural analysis of a structural element, the method comprising:
   receiving information regarding the structural element and a request to perform fatigue and structural analysis upon the structural element;
   automatically performing at least two types of fatigue and structural analysis based upon the information regarding the element and the request without further manual input, wherein automatically performing comprises automatically selecting at least one analysis tool from a plurality of analysis tools to perform the at least two types of fatigue and structural analysis based upon the request; and
   automatically providing results of the fatigue and structural analysis.

2. The method of claim 1, further comprising formatting the information received regarding the structural element prior to performing the fatigue and structural analysis.

3. The method of claim 1, wherein said automatically performing at least two types of fatigue analysis comprises automatically determining a fatigue allowable for the structural element and automatically determining an actual maximum stress for the structural element; and wherein the method further comprises automatically comparing the fatigue allowable and the actual maximum stress and determining a margin of safety for the structural element based upon the comparison.

4. The method of claim 3, wherein automatically determining the fatigue allowable for the structural element comprises determining an anticipated loading of the structural element over time and determining the fatigue allowable to which the structural element may be subjected based upon the anticipated loading of the structural element over time, and wherein automatically determining the actual maximum stress for the structural element comprises determining the actual stress to which the structural element is subjected based upon the application of a reference load.

5. The method of claim 1, further comprising storing the results of the fatigue and structural analysis.

6. The method of claim 1, wherein receiving information regarding the structural element and the request to perform fatigue and structural analysis upon the structural element comprises receiving information regarding the structural element and a request to perform fatigue and structural analysis upon the structural element from a plurality of distributed clients, and wherein the method further comprises transmitting the information regarding the structural element and the request to perform fatigue and structural analysis from the plurality of distributed clients to at least one common processing component via a computer network.

7. The method of claim 6, further comprising presenting at least one web page upon each client to solicit the information regarding the structural element.

8. An automated system for fatigue and structural analysis of a structural element, the system comprising:

a client component capable of receiving information describing the structural element and a request for fatigue and structural analysis of the structural element; and a processing component responsive to said client component and capable of automatically performing the fatigue and structural analysis based upon the information describing the structural element and the request without additional manual input by automatically selecting at least one analysis tool from a plurality of analysis tools to perform the at least two types of fatigue and structural analysis based upon the request, said processing component also capable of automatically providing results of the fatigue and structural analysis to said client component.

9. The system of claim 8, wherein said processing component is further capable of formatting the information for the fatigue and structural analysis.

10. The system of claim 8, wherein said processing component automatically performs the fatigue analysis by:

automatically determining a fatigue allowable for the structural element;

automatically determining an actual maximum stress for the structural element;

automatically comparing the fatigue allowable with the actual maximum stress; and automatically determining a margin of safety for the structural element based upon the comparison.

11. The system of claim 10, wherein said processing component automatically determines the fatigue allowable for the structural element by determining an anticipated loading of the structural element over time and then determining the fatigue allowable to which the structural element may be subjected based upon the anticipated loading of the structural element over time, and wherein said processing component automatically determines the actual maximum stress for the structural element by determining the actual stress to which the structural element is subjected based upon the application of a reference load.

12. The system of claim 8, further comprising a storage element for storing the results of the fatigue and structural analysis.

13. The system of claim 8, wherein said client component and said processing element are remote from one another, and wherein the system further comprises a computer network for interconnecting said client component and said processing element.

14. The system of claim 13, further comprising a plurality of distributed client components interconnected to said processing element via said computer network.

15. The system of claim 14, wherein said processing element comprises a server.

16. The system of claim 13, wherein said client component is capable of presenting at least one web page to solicit the information regarding the structural element.

* * * * *